US012746037B2

(12) United States Patent
Gitelis et al.

(10) Patent No.: US 12,746,037 B2
(45) Date of Patent: Sep. 29, 2026

(54) INJECTION NEEDLE WITH ENDOSCOPE FOR REGENERATIVE MEDICINE

(71) Applicant: PSIP2 LLC, Manchester, NH (US)

(72) Inventors: Michael Gitelis, Barrington, IL (US); Salmaan Hameed, San Jose, CA (US); John M. Cronk, Strafford, NH (US); Bryan Lord, Bedford, NH (US)

(73) Assignee: PSIPZ LLC

( * ) Notice: Subject to any disclaimer, the term of this patent is extended or adjusted under 35 U.S.C. 154(b) by 1295 days.

(21) Appl. No.: 17/151,485

(22) Filed: Jan. 18, 2021

(65) Prior Publication Data

US 2021/0220014 A1 Jul. 22, 2021

Related U.S. Application Data

(60) Provisional application No. 62/962,987, filed on Jan. 18, 2020.

(51) Int. Cl.
*A61B 17/34* (2006.01)
*A61B 1/00* (2006.01)
(Continued)

(52) U.S. Cl.
CPC ...... *A61B 17/3474* (2013.01); *A61B 1/00016* (2013.01); *A61B 1/05* (2013.01);
(Continued)

(58) Field of Classification Search
CPC ............ A61B 1/00096; A61B 1/00179; A61B 1/0661; A61B 1/05; A61B 1/00016;
(Continued)

(56) References Cited

U.S. PATENT DOCUMENTS 4,273,110 A 6/1981 Groux
4,765,313 A 8/1988 Kumakura
(Continued)

FOREIGN PATENT DOCUMENTS

CN 2551172 Y 5/2003
CN 2868212 Y 2/2007
(Continued)

OTHER PUBLICATIONS

PCT/IB2021/050359, Search Report and Written Opinion (May 12, 2021).

(Continued)

*Primary Examiner* — Anh Tuan T Nguyen
*Assistant Examiner* — Li-Ting Song
(74) *Attorney, Agent, or Firm* — Bond, Schoeneck & King, PLLC

(57) ABSTRACT

An injection needle has a point designed to pierce flesh of a living body, and has a fluid passage therethrough designed for delivery of a therapeutic agent at a delivery site within the body, the delivery site to be reached by piercing at which an injection fluid is to be delivered via the fluid passage. The outer diameter of the needle is no more than about 2.1 mm. Solid state illumination circuitry and an imaging sensor are designed to provide illumination and imaging, and are mounted within supporting structure designed to support the illumination circuitry and imaging sensor within the needle arranged for illuminating and viewing the delivery site reached by piercing.

27 Claims, 7 Drawing Sheets

(51) Int. Cl.
*A61B 1/05* (2006.01)
*A61B 1/06* (2006.01)
*A61B 17/00* (2006.01)

(52) U.S. Cl.
CPC ... *A61B 1/0661* (2013.01); *A61B 2017/00115* (2013.01); *A61B 2017/00296* (2013.01)

(58) Field of Classification Search
CPC ...... A61B 17/3474; A61B 2017/00115; A61B 2017/00296; A61M 5/158
See application file for complete search history.

(56) References Cited

U.S. PATENT DOCUMENTS

| | | | | |
|---|---|---|---|---|
| 4,852,551 | A | 8/1989 | Opie | |
| 4,895,138 | A | 1/1990 | Yabe | |
| 4,919,112 | A | 4/1990 | Siegmund | |
| 4,964,710 | A | 10/1990 | Leiner | |
| 4,997,084 | A | 3/1991 | Opie | |
| 5,165,387 | A | 11/1992 | Woodson | |
| 5,188,092 | A | 2/1993 | White | |
| 5,377,047 | A | 12/1994 | Broome | |
| 5,519,532 | A | 5/1996 | Broome | |
| 5,573,493 | A | 11/1996 | Sauer | |
| 5,653,677 | A | 8/1997 | Okada | |
| 5,711,755 | A | 1/1998 | Bonnell | |
| 5,718,664 | A | 2/1998 | Peck | |
| 5,892,630 | A | 4/1999 | Broome | |
| 6,293,910 | B1 | 9/2001 | Yamakita | |
| 6,605,260 | B1 | 8/2003 | Busted | |
| 6,652,452 | B1 | 11/2003 | Seifert | |
| 6,865,825 | B2 | 3/2005 | Bailey | |
| 7,033,317 | B2 | 4/2006 | Pruitt | |
| 7,239,805 | B2 | 7/2007 | Uyttendaele | |
| 7,413,543 | B2 | 8/2008 | Banik | |
| 7,427,262 | B2 | 9/2008 | Bonningue | |
| 7,479,106 | B2 | 1/2009 | Banik | |
| 7,530,946 | B2 | 5/2009 | Hartwick | |
| 7,976,559 | B2 | 7/2011 | Goldfarb | |
| 8,187,170 | B2 | 5/2012 | Naito | |
| 8,257,386 | B2 | 9/2012 | Lee | |
| 8,398,540 | B2 | 3/2013 | Hassidov | |
| 8,449,456 | B2 | 5/2013 | Ueno | |
| 8,556,806 | B2 | 10/2013 | Farr | |
| 8,827,899 | B2 | 9/2014 | Farr | |
| 8,858,425 | B2 | 10/2014 | Farr | |
| 9,066,658 | B2 | 6/2015 | Hamel | |
| 9,107,574 | B2 | 8/2015 | Goldfarb | |
| 9,116,282 | B2 | 8/2015 | Kazakevich | |
| 9,242,069 | B2 | 1/2016 | Alt | |
| 9,271,637 | B2 | 3/2016 | Farr | |
| 9,364,249 | B2 | 6/2016 | Kimball | |
| 9,504,373 | B2 | 11/2016 | Munro | |
| 9,552,577 | B2 | 1/2017 | Di Tucci | |
| 9,877,654 | B2 | 1/2018 | Tesar | |
| 9,895,048 | B2 | 2/2018 | Ouyang | |
| 9,907,457 | B2 | 3/2018 | Grant | |
| 10,105,040 | B2 | 10/2018 | Ochi | |
| 10,278,563 | B2 | 5/2019 | Ouyang | |
| 10,405,886 | B2 * | 9/2019 | Washburn, II | A61B 1/00108 |
| 10,548,633 | B2 | 2/2020 | Ochi | |
| 10,561,302 | B2 | 2/2020 | Henley | |
| 10,780,187 | B2 | 9/2020 | Kang | |
| 10,945,588 | B2 | 3/2021 | Washburn | |
| 11,141,045 | B2 | 10/2021 | Kucharski | |
| 11,185,216 | B2 | 11/2021 | Heni | |
| 11,278,194 | B2 | 3/2022 | Benning | |
| 11,357,593 | B2 | 6/2022 | Komp | |
| 2001/0031115 | A1 | 10/2001 | Chen | |
| 2004/0098040 | A1 | 5/2004 | Taniguchi | |
| 2005/0234294 | A1 | 10/2005 | Saadat et al. | |
| 2006/0149127 | A1 | 7/2006 | Seddiqui | |
| 2006/0276692 | A1 | 12/2006 | Kucklick | |
| 2007/0049794 | A1 | 3/2007 | Glassenberg et al. | |
| 2007/0202005 | A1 | 8/2007 | Maschke | |
| 2007/0225556 | A1 | 9/2007 | Ortiz | |
| 2007/0249904 | A1 | 10/2007 | Amano | |
| 2008/0027283 | A1 | 1/2008 | Matsui | |
| 2008/0051802 | A1 | 2/2008 | Schostek | |
| 2008/0300456 | A1 | 12/2008 | Irion | |
| 2009/0076329 | A1 | 3/2009 | Su | |
| 2009/0082623 | A1 * | 3/2009 | Rothe | A61B 1/00089 600/109 |
| 2009/0082630 | A1 | 3/2009 | Tulley | |
| 2010/0198009 | A1 | 8/2010 | Farr | |
| 2010/0204546 | A1 | 8/2010 | Hassidov | |
| 2011/0009694 | A1 | 1/2011 | Schultz | |
| 2011/0028790 | A1 | 2/2011 | Farr | |
| 2011/0237880 | A1 | 9/2011 | Hamel | |
| 2012/0029280 | A1 | 2/2012 | Kucklick | |
| 2012/0116398 | A1 | 5/2012 | Goldfarb | |
| 2012/0197078 | A1 | 8/2012 | Stanley | |
| 2013/0012783 | A1 | 1/2013 | Vayser | |
| 2013/0253499 | A1 | 9/2013 | Kimball | |
| 2014/0107416 | A1 | 4/2014 | Birnkrant | |
| 2014/0114129 | A1 | 4/2014 | Peh | |
| 2014/0221749 | A1 * | 8/2014 | Grant | A61B 1/00103 600/109 |
| 2014/0243592 | A1 | 8/2014 | Kato et al. | |
| 2014/0275771 | A1 | 9/2014 | Henley | |
| 2015/0011830 | A1 | 1/2015 | Hunter | |
| 2015/0025311 | A1 | 1/2015 | Kadan | |
| 2015/0069728 | A1 | 3/2015 | Seitz, III | |
| 2015/0164313 | A1 | 6/2015 | Ouyang | |
| 2015/0173594 | A1 | 6/2015 | Farhadi | |
| 2015/0327886 | A1 | 11/2015 | Shen | |
| 2015/0374210 | A1 | 12/2015 | Durr | |
| 2016/0235286 | A1 | 8/2016 | Chiang | |
| 2017/0049298 | A1 | 2/2017 | Hunter et al. | |
| 2017/0070654 | A1 | 3/2017 | Ochi | |
| 2017/0078583 | A1 | 3/2017 | Haggerty | |
| 2017/0182194 | A1 | 6/2017 | Shin | |
| 2017/0188795 | A1 | 7/2017 | Ouyang | |
| 2017/0202005 | A1 | 7/2017 | Madan | |
| 2017/0209030 | A1 * | 7/2017 | Nakao | A61B 1/0055 |
| 2017/0245890 | A1 | 8/2017 | Ochi et al. | |
| 2018/0084986 | A1 | 3/2018 | Ochi | |
| 2018/0168442 | A1 | 6/2018 | Schaeffer | |
| 2018/0235441 | A1 | 8/2018 | Huang | |
| 2018/0296281 | A1 | 10/2018 | Yeung et al. | |
| 2018/0317762 | A1 | 11/2018 | Fowler et al. | |
| 2019/0038116 | A1 | 2/2019 | Ochi | |
| 2019/0216300 | A1 * | 7/2019 | Levy | A61B 1/00177 |
| 2019/0298151 | A1 | 10/2019 | Frangioni | |
| 2019/0321077 | A1 * | 10/2019 | Kienzle | A61B 17/3478 |
| 2019/0328217 | A1 | 10/2019 | Moreau | |
| 2019/0374095 | A1 | 12/2019 | Lord | |
| 2020/0000491 | A1 | 1/2020 | Washburn | |
| 2020/0214543 | A1 * | 7/2020 | Ben-Arye | A61B 1/00103 |
| 2020/0222146 | A1 | 7/2020 | Komp | |
| 2020/0345218 | A1 | 11/2020 | Lord | |
| 2020/0397232 | A1 * | 12/2020 | Ulmschneider | H04N 23/54 |
| 2021/0052145 | A1 | 2/2021 | Rauniyar | |
| 2021/0113068 | A1 | 4/2021 | Shin et al. | |
| 2021/0169316 | A1 | 6/2021 | Schultheis | |
| 2021/0220014 | A1 | 7/2021 | Gitelis | |
| 2021/0330177 | A1 | 10/2021 | Kohno | |
| 2022/0125280 | A1 | 4/2022 | Tyan | |
| 2022/0378279 | A1 | 12/2022 | Poll | |
| 2023/0123867 | A1 | 4/2023 | Herda et al. | |

FOREIGN PATENT DOCUMENTS

| | | | |
|---|---|---|---|
| CN | 101040775 | | 9/2007 |
| CN | 101801278 | | 8/2010 |
| CN | 103315807 | | 9/2013 |
| CN | 106308727 | | 1/2017 |
| CN | 106821285 | | 6/2017 |
| CN | 107157429 | | 9/2017 |
| CN | 111458859 | | 7/2020 |
| DE | 10330177 | A1 | 3/2005 |
| EP | 0904725 | B1 | 9/2005 |
| EP | 1634656 | A1 | 3/2006 |

(56) References Cited

FOREIGN PATENT DOCUMENTS

| | | | |
|---|---|---|---|
| EP | 1902665 | A1 | 3/2008 |
| EP | 2266452 | | 12/2010 |
| EP | 4090270 | A1 | 11/2022 |
| JP | 2001-128923 | A | 5/2001 |
| JP | 2002-512086 | | 4/2002 |
| JP | 2004-358107 | | 12/2004 |
| JP | 2007020797 | A | 2/2007 |
| JP | 4315489 | B2 | 8/2009 |
| JP | 2014066923 | A | 4/2014 |
| JP | 2013-192953 | | 9/2018 |
| JP | 2019515762 | A | 6/2019 |
| KR | 20030073761 | A | 9/2003 |
| KR | 10-1614939 | | 4/2016 |
| KR | 20160044635 | A | 4/2016 |
| KR | 10-1784213 | | 10/2017 |
| KR | 20180041759 | A | 4/2018 |
| WO | WO1993/015648 | A2 | 8/1993 |
| WO | WO2006/073676 | A1 | 7/2006 |
| WO | WO2012/027581 | A2 | 3/2012 |
| WO | WO2014/031192 | A1 | 2/2014 |
| WO | WO2015/142720 | A1 | 9/2015 |
| WO | WO2017/040692 | A1 | 3/2017 |
| WO | WO2017/147605 | | 8/2017 |
| WO | WO2017/147605 | A1 | 8/2017 |
| WO | WO2019/234712 | A1 | 12/2019 |
| WO | WO 2021/144778 | | 7/2021 |
| WO | WO2021/161228 | | 8/2021 |
| WO | WO2022/003569 | | 1/2022 |
| WO | WO2023/026257 | A1 | 3/2023 |
| WO | WO2023/053042 | A1 | 4/2023 |

OTHER PUBLICATIONS

Martín Arranz et al., *Endoscopic submucosal injection of adipose-derived mesenchymal stem cells ameliorates TNBS-induced colitis in rats and prevents stenosis*, Stem Cell Research & Therapy 9:95 doi 10.1186/s13287-018-0837-x (Apr. 10, 2018).

Hoogduijn & Lombardo, *Mesenchymal Stromal Cells Anno 2019: Dawn of the Therapeutic Era? Concise Review*, Stem Cells Translational Medicine 8(11):1126-1134, doi: 10.1002/sctm.19-0073 (Jul. 7, 2019).

Kehoe et al., *Intra-articular injection of mesenchymal stem cells leads to reduced inflammation and cartilage damage in murine antigen-induced arthritis*, J. Translational Medicine 12:157, doi: 10.1186/1479-5876-12-157 (Jun. 3, 2014).

Kracutler et al., *The use of platelet-rich plasma to augment conservative and surgical treatment of hip and pelvic disorders*, Muscles, Ligaments and Tendons J. 6(3):409-419, doi: 10.11138/mltj/2016.6.3.410 (Dec. 21, 2016).

Mazzanti et al., *Local injection of bone marrow progenitor cells for the treatment of anal sphincter injury: in-vitro expanded versus minimally-manipulated cells*, Stem Cell Research & Therapy 7:85 DOI 10.1186/s13287-016-0344-x (Jun. 21, 2016).

Mirzayan et al., *Carbon Dioxide Insufflation of the Knee in the Treatment of Full-Thickness Chondral Defects With Micronized Human Articular Cartilage*. Arthroscopy Techniques, 7(10):e969-e973, doi: 10.1016/j.eats.2018.05.005 (Oct. 2018).

NanoSurgery Technology Corp., Product Technology, Introducing the Nanoscope, http://nanosurgerytech.com/product-technology (retrieved Jul. 25, 2019).

Trice Medical, *mi-eye 2 is the revolutionary alternative to a tradidioal MRI*, https://tricemedical.com/mi-eye (retrieved Jul. 25, 2019).

India App. 202027054048, Hearing Notice (May 1, 2024).

Canada App. 3,102,585, Office Action (Oct. 6, 2023).

PCT/IB2021/04359, International Preliminary Report on Patentability (Mar. 4, 2022).

Canada App. 3,165,314, Office Action (Oct. 18, 2023).

China App. CN 201980038145.1 , Office Action (Feb. 14, 2023).

Japan App. 2020-567600; Office Action (Aug. 15, 2023).

Oksana Kehoe, Alison Cartwright, Ayman Askari, Alicia J El Haj, and Jim Middleton: Intra-articular injection of mesenchymal stem cells leads to reduced inflammation and cartilage damage in murine antigen-induced arthritis, Journal of Translational Medicine 12:157, doi: 10.1186/1479-5876-12-157 (Jun. 3, 2014).

Benedetta Mazzanti, Bruno Lorenzi, Annalisa Borghini, Margherita Boieri, Lara Ballerini, Riccardo Saccardi, Elisabetta Weber, and Federica Pessina: Local injection of bone marrow progenitor cells for the treatment of anal sphincter injury: in-vitro expanded versus minimally-manipulated cells, Stem Cell Research & Therapy 7:85, doi 10.1186/s13287-016-0344-x (Jun. 21, 2016).

Raffy Mirzayan, Joseph D. Cooper, and Jorge Chahla, Carbon Dioxide Insufflation of the Knee in the Treatment of Full-Thickness Chondral Defects With Micronized Human Articular Cartilage, Arthroscopy Techniques, 7:10:e969-e973, doi: 10.1016/j.eats.2018.05.005 (Oct. 2018).

Martin J. Hoogduijn, Eleuterio Lombardo, Concise Review: Mesenchymal Stromal Cells Anno 2019: Dawn of the Therapeutic Era? Stem Cells Translational Medicine 00:1-9 doi: 10.1002/sctm.19-0073 (2019).

NanoSurgery Technology Corp., Product Technology, Introducing the NanoScope, http://nanosurgerytech.com/product-technology/ (accessed Sep. 15, 2019).

Trice Medical, Mi-eye 2 is the revolutionary alternative to a traditional MRI, https://tricemedical.com/mi-eye/ (accessed Jul. 25, 2019).

PCT/IB2021/050359, Article 34 Amendment (excerpts) (Nov. 18, 2021).

PCT/IB2021/050359, International Preliminary Report on Patentabilty (Chapter II) (Mar. 4, 2022).

PCT/IB2021/050359, ISA/210 International Search Report, and ISA/237 Written Opinion of the International Searching Authority (May 18, 2021).

PCT/IB2019/054783 , ISA/210 International Search Report and ISA/237 Written Opinion of the International Searching Authority (Oct. 24, 2019).

PCT/IB2021/055823, Article 34 Amendment (Mar. 30, 2022).

PCT/IB2021/055823, ISA/210 International Search Report and ISA/237 Written Opinion (Aug. 10, 2021).

PCT/IB2021/055823, Written Opinion (May 16, 2022).

PCT/IB2022/054938, International Search Report and Written Opinion of the International Searching Authority (Nov. 29, 2022).

PCT/IB2022/058030, Article 34 Amendment (Mar. 19, 2023).

PCT/IB2022/058030, ISA/210 Search Report and ISA/237 Written Opinion of the International Searching Authority (Dec. 19, 2022).

PCT/IB2022/059262, ISA/210 International Search Report and ISA/237 Written Opinion of the International Searching Authority (Dec. 14, 2022).

China App. CN 201980038145.1 , Office Action with Search Report (Jun. 23, 2022).

China App. CN 201980038145.1 , Reply to Office Action (Nov. 8, 2022).

China App. CN 201980038145.1 , Office Action (Nov. 17, 2022).

EPO App. EP 19 746 152.8 , Communication pursuant to Article 94(3) EPC (Sep. 28, 2021).

EPO App. EP 19746152.8 , Reply to Communication pursuant to Article 94(3) (Feb. 7, 2022).

EPO App. EP 19746152.8 , Extended European Search Report (Dec. 21, 2022).

EPO App. EP 19746152.8 , Communication pursuant to Article 94(3) EPC (Mar. 17, 2023).

Japan App. 2020-567600 , Office Action (Mar. 7, 2023).

Steffi Sunny, George Cheng, Daniel Daniel, Peter Lo, Sebastian Ochoa, Caitlin Howell, Nicolas Vogel, Adnan Majid, Joanna Aizenberg, *Transparent antifouling material for improved operative field visibility in endoscopy*, Proceedings of the National Academy of Sciences U.S.A., Oct. 18, 2016;113(42):11676-11681. doi: 10.1073/pnas.1605272113 (Sep. 29, 2016).

Matthew J. Kraeutler, Tigran Garabekyan, Omer Mei-Dan, The use of platelet-rich plasma to augment conservative and surgical treatment of hip and pelvic disorders, Muscles, Ligaments and Tendons Journal 410 2016;6 (3):409-419 doi: 10.11138/mltj/2016.6.3.410 (Dec. 21, 2016).

(56) References Cited

OTHER PUBLICATIONS

Felix Asche, Basler AG, White Paper, Modern CMOS Sensors and Their Use in Fluorescence-Based Applications (Nov. 2017).
Eduardo Martín Arranz, María Dolores Martín Arranz, Tomás Robredo, Pablo Mancheño-Corvo, Ramón Menta, Francisco Javier Alves, Jose Manuel Suárez de Parga, Pedro Mora Sanz, Olga de la Rosa, Dirk Büscher, Eleuterio Lombardo, and Fernando de Miguel: Endoscopic submucosal injection of adipose-derived mesenchymal stem cells ameliorates TNBS-induced colitis in rats and prevents stenosis, Stem Cell Research & Therapy 9:95, doi: 10.1186/s13287-018-0837-x (Apr. 10, 2018).
René von Fintel, Basler AG, White Paper, Modern CMOS Cameras as Replacements for CCD Cameras (May 2018).
Adaptive Surface Technologies, Inc., *AST has brought two distinct product groups to market,* https://adaptivesurface.tech (retrieved May 21, 2021).
Harvard University, Hansjörg Wyss Institute for Biologically Inspired Engineering at Harvard University, *TLP: A Non-Stick Coating for Medical Devices,* https://wyss.harvard.edu/technology/tlp-a-non-stick-coating-for-medical-devices (retrieved May 21, 2021).
EPO App. 19746152.8, Communication pursuant to Article 94 (Nov. 14, 2023).
EPO App. 21741290.7, Extended European Search Report (Dec. 18, 2023).
PCT/IB2022/058030, International Preliminary Report on Patentability (Dec. 24, 2023).
PCT/IB2023/059287, International Search Report and Written Opinion (Dec. 28, 2023).
Japan App. 2020-567600, Office Action (Nov. 28, 2023).
PCT/IB2021/050359, Form ISA/210, International Search Report, and ISA/237 Written Opinion of the International Searching Authority (May 18, 2021).
Oksana Kehoe, et al.: Intra-articular injection of mesenchymal stem cells leads to reduced inflammation and cartilage damage in murine antigen-induced arthritis, Journal of Translational Medicine 12:157, doi: 10.1186/1479-5876-12-157 (Jun. 3, 2014).
Benedetta Mazzanti, et al.: Local injection of bone marrow progenitor cells for the treatment of anal sphincter injury: in-vitro expanded versus minimally-manipulated cells, Stem Cell Research & Therapy 7:85, doi 10.1186/s13287-016-0344-x (Jun. 21, 2016).
Eduardo Martín Arranz, et al.: Endoscopic submucosal injection of adipose-derived mesenchymal stem cells ameliorates TNBS-induced colitis in rats and prevents stenosis, Stem Cell Research & Therapy 9:95, doi: 10.1186/s13287-018-0837-x (Apr. 10, 2018).

* cited by examiner

INJECTION NEEDLE WITH ENDOSCOPE FOR REGENERATIVE MEDICINE

BACKGROUND

This application is a nonprovisional of U.S. Provisional application 62/962,987 filed Jan. 18, 2020, incorporated by reference.

This application relates to endoscopes and injection needles, or processes specially adapted or intended to be used for evaluating, examining, or treating human or animal bodies for medical purposes.

In medical treatments by injection of stem cells, platelet enriched plasma treatments, exosomes, and similar biologicals, it is known to position an injection needle based on ultrasound and the physician's knowledge of human anatomy, and inject the biological into the general region of the pathology. The injected biological then marshals the body's own healing systems to repair the pathology.

SUMMARY

In general, in a first aspect, the invention features an injection needle. The needle has a point designed to pierce flesh of a living body, and has a fluid passage therethrough designed for delivery of a therapeutic agent at a delivery site within the body, the delivery site to be reached by piercing at which an injection fluid is to be delivered via the fluid passage. The outer diameter of the needle is no more than about 2.1 mm. Solid state illumination circuitry and an imaging sensor are designed to provide illumination and imaging, and are mounted within supporting structure designed to support the illumination circuitry and imaging sensor within the needle arranged for illuminating and viewing the delivery site reached by piercing.

In general, in a second aspect, the invention features a method. A patient is pierced with a needle. The needle has a point designed to pierce flesh of a living body, and having a fluid passage therethrough designed for delivery of a therapeutic agent at a delivery site within the body, the delivery site to be reached by piercing is a site at which an injection fluid is to be delivered via the fluid passage, the outer diameter of the needle being no more than about 2.1 mm. The needle surrounds solid state illumination circuitry and an imaging sensor designed to provide illumination and imaging, mounted within supporting structure designed to support the illumination circuitry and imaging sensor within the needle arranged for illuminating and viewing flesh ahead of the point of the needle during the piercing. When the point of the needle reaches the delivery site, insufflation fluid is passed through a passage of the needle to inflate a cavity at the delivery site. The supporting structure is extended forward through the needle, sufficiently to create a field of view for the imaging sensor wider than the field of view available during the piercing. The imaging sensor and illumination circuitry are rotated around a longitudinal axis of the needle, a rotation or orientation sensor rotationally affixed to the imaging sensor being designed to produce a signal that encodes angular rotation of the image sensor. The video from the image sensor and the encoded angular rotation signal are processed together in image-righting circuitry to compute a corrected video signal that corrects the video signal for rotation to present a video signal consistently oriented relative to a frame of reference of a user of the injection needle.

Embodiments of the invention may include one or more of the following features. These features may be used singly, or in combination with each other. The image sensor may have an axis of view offset from the axis of the needle. The image sensor may be mounted within the supporting structure with its axis of view offset from the axis of the needle. The image sensor may be mounted within the supporting structure with the camera's axis of view parallel to the axis of the needle. A lens may be designed and mounted within the supporting structure to refract an image received by the image sensor off the axis of the needle. The angle of offset may desirably be between about 25° and about 35°, or between about 65° and about 75°. Two or more supporting structures may be designed to support imaging sensors so as to provide different angles of offset for the imaging sensors' fields of view relative to the axis of the needle. A rotation or orientation sensor may be designed to produce a signal that encodes angular rotation of the image sensor. Circuitry may be designed to receive the encoded angular rotation signal and a video signal from the image sensor, and to compute a corrected video signal that corrects the video signal for rotation to present a video signal consistently oriented relative to a frame of reference of a user of the injection needle. Wireless transmission circuitry may be designed to transmit video signal from the imaging sensor to a display monitor without transmission wires connected to the injection needle. One or more reservoirs may be designed to hold insufflation fluid. Controls may be designed to administer the fluid without fluid tubes flowing externally to the injection needle. A piercing point distal from the imaging sensor may be designed to pierce flesh and to simultaneously provide protection to the imaging sensor from the flesh and its fluids, and to allow an image of the flesh to reach the imaging sensor. The outer diameter of the needle may desirably be no more than about 1.66 mm, no more than about 1.28 mm, no more than about 0.91 mm, no more than about 0.82 mm. A proximal portion of a handle may have electronics for drive of the illumination circuitry and to receive imaging signal from the imaging circuitry, the proximal handle portion being designed to permit sterilization between uses. A joint between the proximal handle portion and the needle and supporting structure may be designed to separably connect the needle and supporting structure to the proximal handle portion. The joint may permit removal of the supporting structure for disposal and replacement. The joint, when connected, may be designed to provide mechanical force transfer between a surgeon's hand to the needle, and electrical connectivity between the proximal handle circuitry and the illumination circuitry and imaging sensor. The supporting structure may be slideable within the needle to permit the imaging sensor to be retracted behind the point during the piercing, and to be extended beyond the point to obtain a wider field of view. The patient may be human or animal.

The above advantages and features are of representative embodiments only, and are presented only to assist in understanding the invention. It should be understood that they are not to be considered limitations on the invention as defined by the claims. Additional features and advantages of embodiments of the invention will become apparent in the following description, from the drawings, and from the claims.

DESCRIPTION

I. Overview

Figures 1A, 1B, 1C:
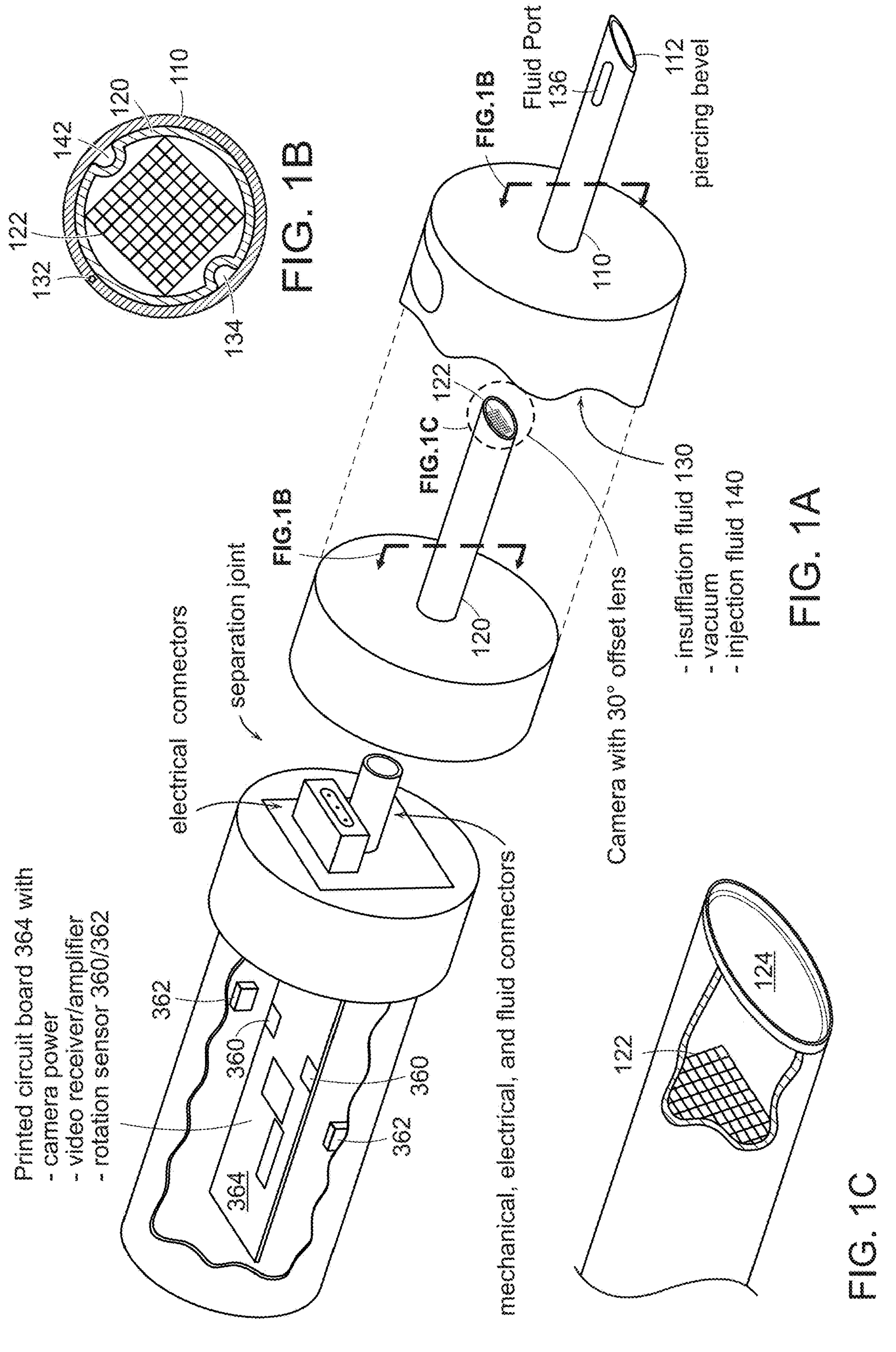
FIGS. 1A, 1C, 2A. 2B, 3B, 3C, 4A. and 4B are perspective views partially cut away.
FIGS. 1B and 3A, are plan sectional views.

Referring to FIGS. 1A and 1B, in regenerative medicine, a suspension of some orthobiologic agent, such as stem cells, exosomes, platelet enriched plasma, BMAC (bone marrow aspirate concentrate), anti-inflammatory factors, or similar biologic component, is injected into a body at the site of a lesion or pathology to be treated. The higher the number of cells, components, etc. that can be placed on target, the higher the likelihood of success. Therefore, an injectable agent may be prepared by concentrating the cells, exosomes, etc. to a high concentration, which may be administered by needle/scope 100 that is designed to allow precise placement. An injection needle 110 with a piercing point 112 may be combined with an endoscope 120, or otherwise fitted with an image sensor 122, to allow injection needle/scope 100 to be guided precisely to the pathology, to increase the concentration of the injected biologic agent at the precise site.

Among the advantages that may be realized are the following. The techniques and apparatus may be useful for cartilage resurfacing, placement of stem cells to regenerate some tissue (such as pancreas or liver cells), foster bone or marrow regeneration, and the like. The technique and apparatus may improve a physician's ability to deliver biologic agents at the site of pathology. This may allow for a greater concentration of proteins (biologic or synthetic) to be delivered at the pathological site. The higher concentration of proteins may modulate and block inflammation, and deliver growth and healing factors to the site. More-precise delivery may reduce pain by blocking inflammation and reducing the distension/disruption of tissue caused by larger injection deliveries, his, in turn, may permit reduction in use of opioids, by an estimated 70%. More-precise delivery may permit delivery of proteins that can promote faster and more organized healing. In addition, greater signaling via exosomes may be sent to cells (induction), to obtain a longer therapeutic effect. The technique and apparatus, especially the small size and minimization of tissue damage, may reduce injury and improve healing, which may allow more procedures to be done as orthobiologic injection in the physician's office, rather than a surgical center, which may reduce costs. The needle tip 112, 122 may be designed to provide standard placement and provide a good field of view, via rotation about its roll axis, which may reduce tissue damage and pain to the patient. Various techniques for enhancing view through rotation are discussed in section IV below.

II. Preparation and Administration of Biologic Agents

A typical injection of a biologic begins with a draw from the patient, to prepare an autologous injection. For example, a typical blood draw from a patient of 5-6 cc has about 5 million stem cells, approximately 900,000 stem cells per cc Those stem cells may be concentrated by centrifuging or other separation means.

Referring to FIGS. 1A and 1B, administration of the concentrated biologic may be by means of injection needle/scope 100 designed to permit precise placement. Camera 122 may be mounted in endoscope shaft 120, and camera shaft 120 inserted through cannula 110. Cannula 110 and camera 122 may be inserted into a patient. Camera 122 may be retracted within cannula 110 during the piercing phase of the injection, so that cannula tip 112 does the cutting, and camera 122 is protected. When used to inject into a joint, cannula tip 112 cuts an injection pathway until the capsule around the joint is pierced. In some cases, needle 110 may contain a rigid support element during the piercing to provide strength and rigidity, and then this rigid support element may be withdrawn and replaced by camera 122 and camera shaft 120 when the needle is placed approximately, so that camera 122 may be used to guide the needle to a precise delivery site. Camera shaft 120 may then be advanced to extend slightly beyond the tip of the cannula, to allow camera 122 an unobstructed view, and to reduce risk that the sharp tip 112 of the cannula will injure cartilage within the joint. Gas 130 (typically carbon dioxide) may be used to insufflate the field of view for camera 122, to blow blood and other debris off the camera lens or window 124, and to dry the area to improve view and to decrease flow and improve the localization of the injectate. Likewise, water 130 may be injected into the site for insufflation/expansion of the joint, and for cleaning of window 124. The insufflation fluid (liquid or gas) 130 may pass through an annulus 132 between the outer diameter of camera shaft 120 and inner diameter of cannula 110 if camera shaft 120 is slightly smaller than the inner diameter of cannula 110, or camera shaft 120 may have a "dimple" of a channel in its outer edge that carries insufflation fluid 130. Cannula 110 may have ports 136 somewhat proximal of the tip, to reduce image blurring that might be caused by insufflation delivery closer to camera 122. If camera shaft 120 has a groove 134 for passage of insufflation fluid 130, that passage may spiral around the shaft, or it may branch into several circumferential channels, so that the insufflation channel 134 will always line up with insufflation ports 136. Camera 122 may guide the injection surgeon to the site of the pathology. At the site of the pathology, gas 130 may be blown to create a volume to improve visibility, and to dry the site. Camera shaft 120 may be withdrawn, leaving the cannula tip 112 at the site of the pathology. Alternatively, camera shaft 120 may have a lumen through which the injectable biologic 140 or other fluid may be delivered to the desired site, or may provide a passage/groove between camera shaft 120 and cannula for conduct of fluids. To the degree that blown gas 130 is not drawn off by withdrawal of camera 122, and does not escape on its own, further gas 130 may be removed by vacuum. Then concentrated biologic or other injectable fluid 140 may be injected through the cannula 110.

III. Injection Scope

Figure 2A:
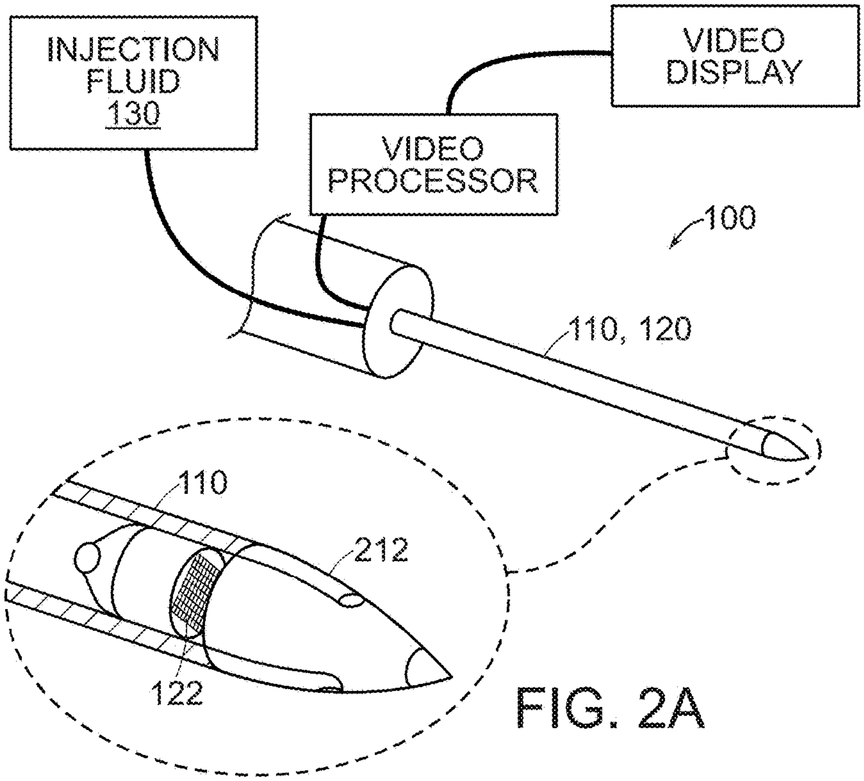
Figure 2B:
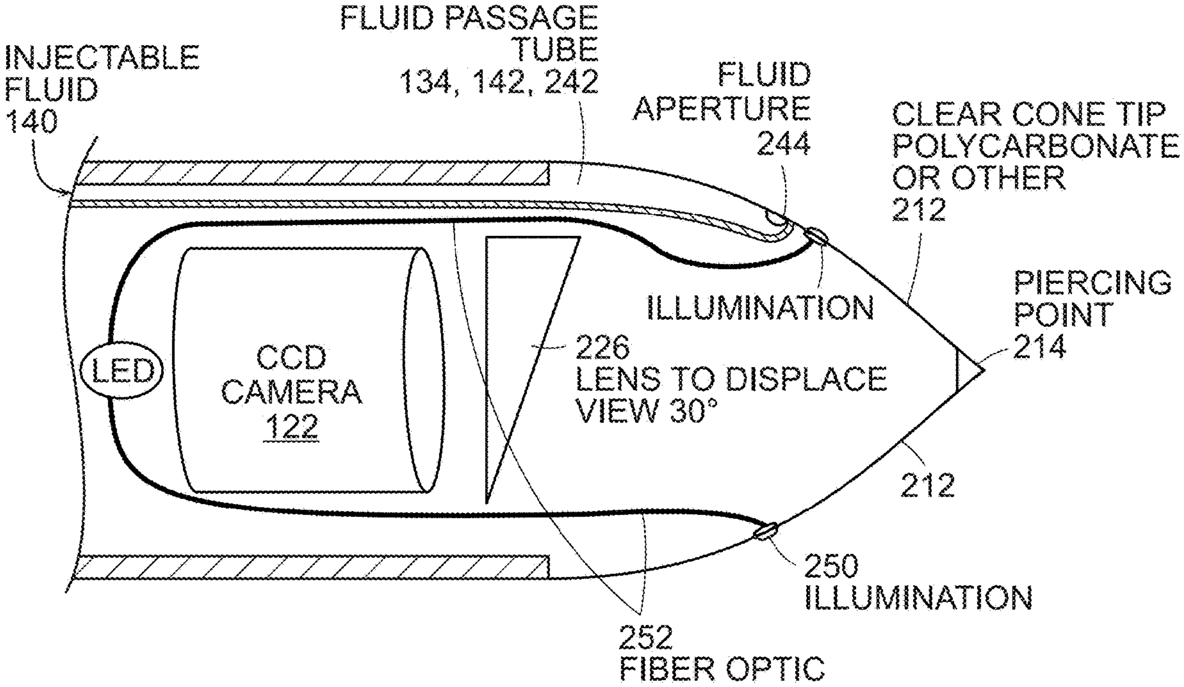

Referring to FIGS. 2A and 2B, needle/scope 100 may incorporate functions of an endoscope and injection needle (with its penetrating tip and fluid passages), integrating camera shaft 120, piercing cannula 110, 112, insufflation passage 134, and delivery needle (or any two or three of these functions) into a single integrated device. The cannula/needle 110 may have a piercing point 112, and camera 122 may be recessed behind that point. The needle may have a channel that can pass the biologic concentrate while camera 122 remains at the site where the injection is to be delivered. Wires may supply power to and receive video signal from camera 122.

Needle/scope 100 may be formed around a hollow metal shaft 110. At or near the tip may be an imaging camera 122. The tip 212 of the needle may be formed from a clear material in a roughly conical shape. Tip 212 may be sharpened to provide a cutting/penetrating tip 214. Rearwards of the cutting tip 214 may be LEDs 250 to provide illumination. Alternatively, an illuminating LED may be somewhat rearward, and light may be conveyed from the LED to the front 250 of the device through light fibers 252. A tube 242 for carrying injectable fluid 140 may end at an exit aperture 244 near the tip. Likewise, a tube for carrying insufflation and cleaning gas (which may be the same as the tube for injectable fluid, or different) may end at an exit aperture near the tip.

The needle may be of diameter of an injection needle, such as less than 2.1 mm (14 gauge), 1.6 mm (16 gauge), 1.47 mm (17 gauge), 1.27 mm (18 gauge), 1.07 mm (19 gauge), or 0.91 mm (20 gauge).

| Gauge | Needle O.D. (mm) | Needle I.D. (mm) | Wall Thickness (mm) |
|---|---|---|---|
| 22 gauge | 0.718 | 0.413 | 0.152 |
| 21 gauge | 0.819 | 0.514 | 0.152 |
| 20 gauge | 0.908 | 0.603 | 0.152 |
| 18 gauge | 1.27 | 0.838 | 0.216 |
| 16 gauge | 1.651 | 1.194 | 0.229 |
| 14 gauge | 2.109 | 1.6 | 0.254 |

Smaller diameters may reduce pain. Smaller diameters may be especially important in arthroscopic surgery, where the working area between bones is confined, between hard structures such as bone and cartilage. An image sensor 122 that is 1 mm×1 mm has a diagonal dimension of 1.4 mm, leaving sufficient gaps around the four edges for fluid passages 134, 142. With the thickness of the walls of an injection needle, the outer diameter may end up at about 1.65 mm, about the same size as a 16 gauge needle.

Figure 3A:
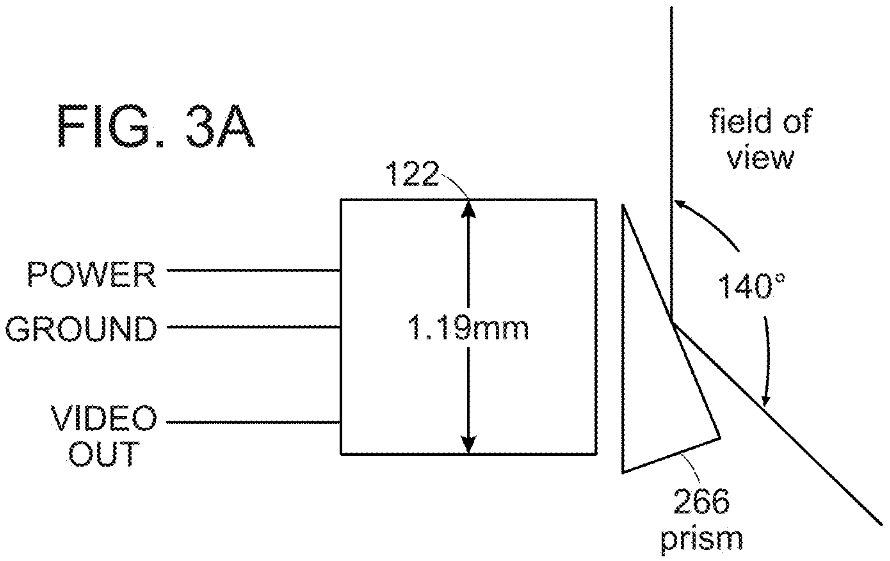

Referring to FIG. 3A, one suitable camera is the OmniVision OV6946, a 400×400 image sensor, 714×707 μm, in a package whose external dimensions are 950×940 μm. As smaller cameras become available, the size of the needle may be reduced as well. The field of view of the OV6946 is about 140°. A lens 226 may be placed in front of camera 122 to offset that field of view by 30° off the central axis. Camera 122 and/or lens 226 may be adjustable so that the offset may be varied, for example, between 0° to 30°, or 300 to 70°.

In some cases, the injection scope may have a passage for inflation by gas or saline 130. Carbon dioxide may be especially desirable as an inflation medium, because of its optical properties, it and it may create a dry environment to confine any tendency of the aqueous biologic agent to flow away. Carbon dioxide, nitric oxide, or another gas may be blown across the front of objective lens 124 of the scope for cleaning, and to blow away smoke and debris created by other instruments. The passage for insufflation gas 134 may be the same as the channel for passage of injection fluid 142, or may be separate.

IV. Increasing Available View Through Rotation of Needle/Scope 100

In manipulating the delivery needle/cannula, it may be desirable to minimize off-axis movement. Forward piercing thrust on a single line is a necessary evil in any injection, but it is desirable to minimize sweep back-and-forth movement, or pitch/yaw bending/rotation. Only roll motion, rotation around the axis, is nondestructive to surrounding tissue. Several techniques may be used to enhance the available view through rotation, to reduce the surgeon's need for other, more-destructive motions.

IV.A. Angular Offset of Image Lens 226

Figure 3B:
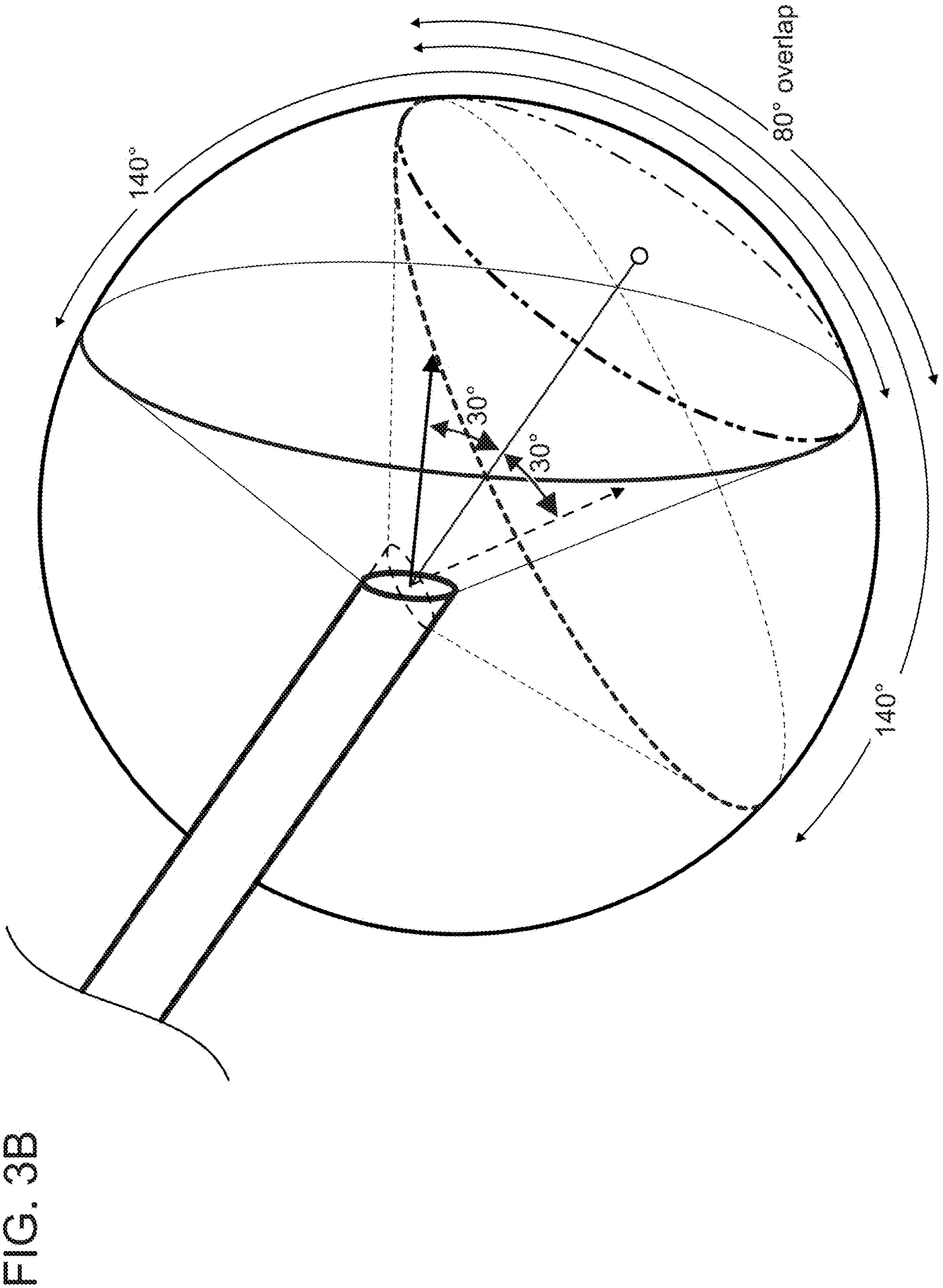

Referring to FIGS. 2B, 3A, 3B, camera 122 of the injection scope may have a lens 226, or may be mounted within needle/scope 100, to provide a view that is offset relative to the longitudinal axis, for example, by 20°, 25°, 30°, 35°, 40°, 45°, 60°, or 70°. By offsetting the angle of view, the scope may be rotated on-axis to cover greater total field of view.

Referring to FIG. 3B, camera 122 may have a cone of view of 140°, 70° off-center in each direction, subtending a portion of the full 360° view. If camera 122 is placed at a 30° offset within the scope, or its view is refracted 226 by 30°, then a forward cone of view of 80° is visible from any orientation. By rotating needle/scope 100 on-axis (the roll axis), then the forward 200° is visible. A 30° offset, plus rotation of the scope may more than double the available field of view.

IV.B. Image Righting

Figure 3C:
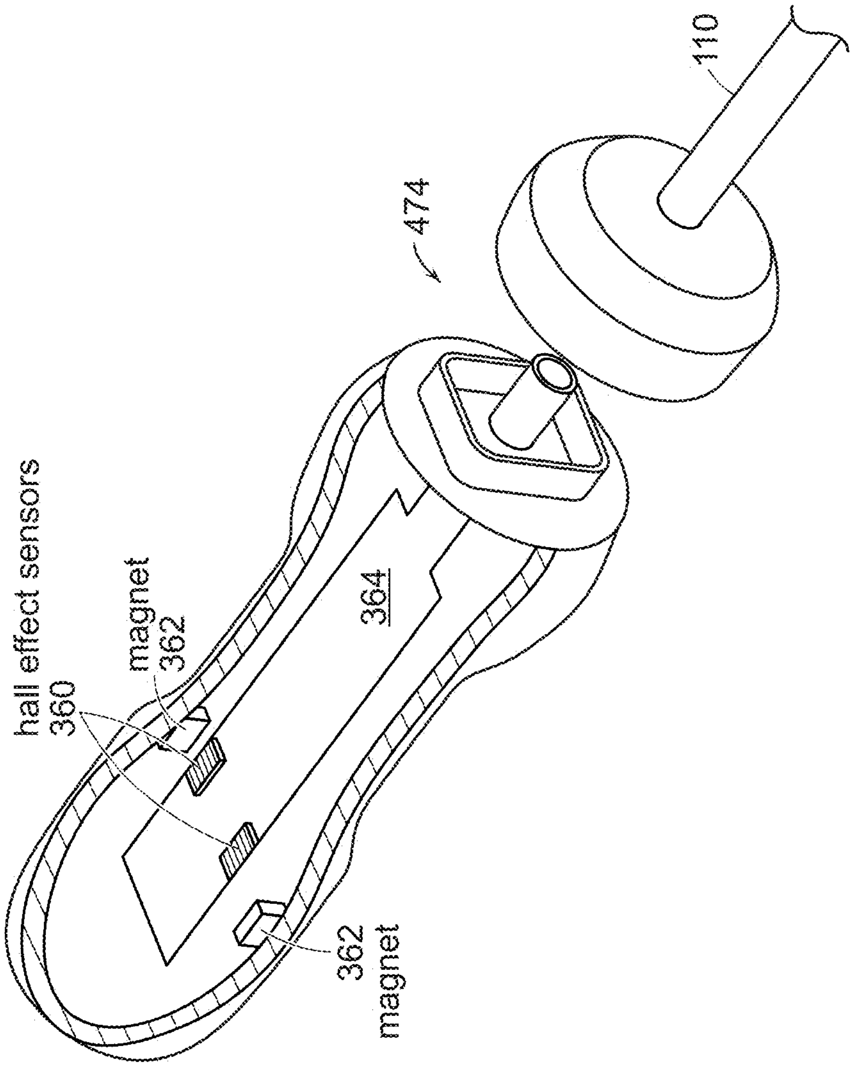

Referring to FIG. 3C, proximal handle may include rotational sensors 360 so that an angular orientation of camera 122 may be ascertained. For example, the inner surface of proximal handle may mount one or more magnets 362, and printed circuit board 364 (which rotates with rotation collar 460 and disposable portion 470) may have Hall effect sensors 360 that detect the magnets. Alternatively, the handle may have a level, gravitometer or other sensor that detects orientation. This may be used to compute a rotational orientation, which may in turn be used to "right" the image from camera 122 on a video display screen. For example, the image may be rotated for display so that the display from a camera that is being rotated behaves similarly to the image in a rod-lens scope, where the image remains rotationally stationary as the scope is rotated. Unless the orientation of an image displayed on a graphical user interface is first corrected, the displayed image may be disorienting to the user. By defining a direction according to the user's point of view, the image processing unit may use data from the rotational sensors to automatically rotate images so that images correspond with the user's point of view. This assists the surgeon in maintaining spatial awareness and making fine motion without injuring the patient.

In some cases, image processing unit may also correct for the effects of lens distortion.

IV.C. Reducing Tethering by Wireless Connection

The injection scope may be cordless/tetherless to improve a surgeon's ability to maneuver the injection scope. The injection scope may communicate image information to a base station imaging unit via a wireless connection, such as WiFi or Bluetooth. The image may be displayed on a display screen in the surgeon's field of view, driven by an image processing and control computer. Injection scope 100 may have a battery to supply power. The injectable fluid, typically 3 to 6 ccs, may be stored in a small reservoir. If insufflation 130 is by means of carbon dioxide, carbon dioxide may be supplied in a cartridge, for example a medical version of a conventional $CO_2$ cartridge. 30 to 60 ccs of insufflation water or saline may be stored in an on board reservoir.

Reducing tethers may improve the surgeon's ability to rotate needle/scope 100, and may improve sterility by reducing cable flop and contact between nonsterile cables and the patient.

IV.D. Reducing Torque Mass by Reducing Rotational Moment

Figure 4A:
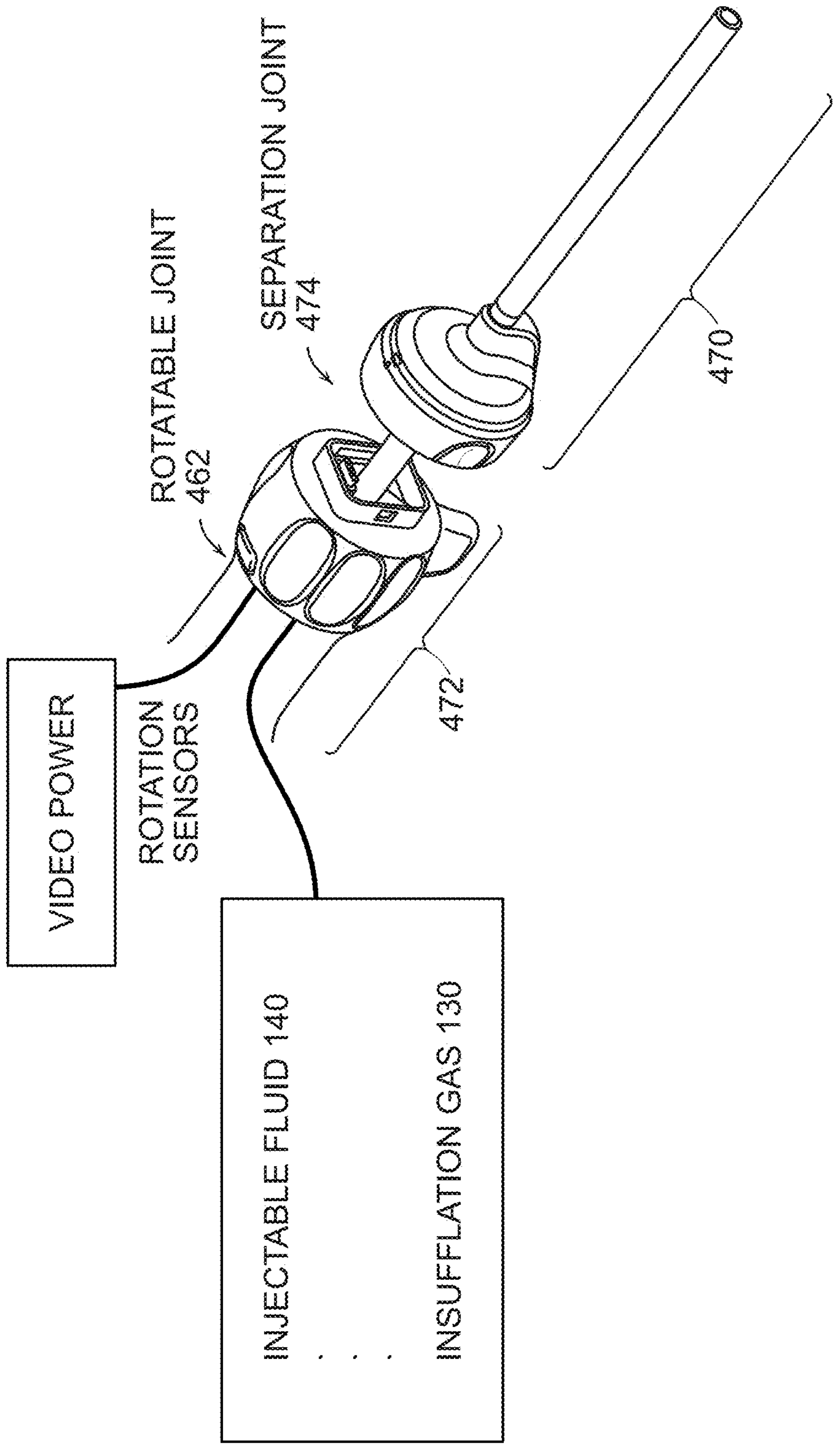

Referring to FIG. 4A, the body of the injection scope may have a rotation joint 462 so that needle/scope 100 (with its camera at the tip) may be rotated, while the main body of the injection scope remains stationary. Any cords or hoses for power or fluids may be attached to the stationary part of the injection scope, to ease rotation.

It may be desirable to put as much of the mass of the battery, fluid reservoirs, and any remaining tethers in the stationary part of the scope. Of the mass that must rotate, it may be desirable to concentrate that mass on the axis of needle/scope 100, to reduce the rotational moment and "flopping" of any remaining cords.

V. Disposable Camera Shaft

V.A. Overview

Figure 4B:
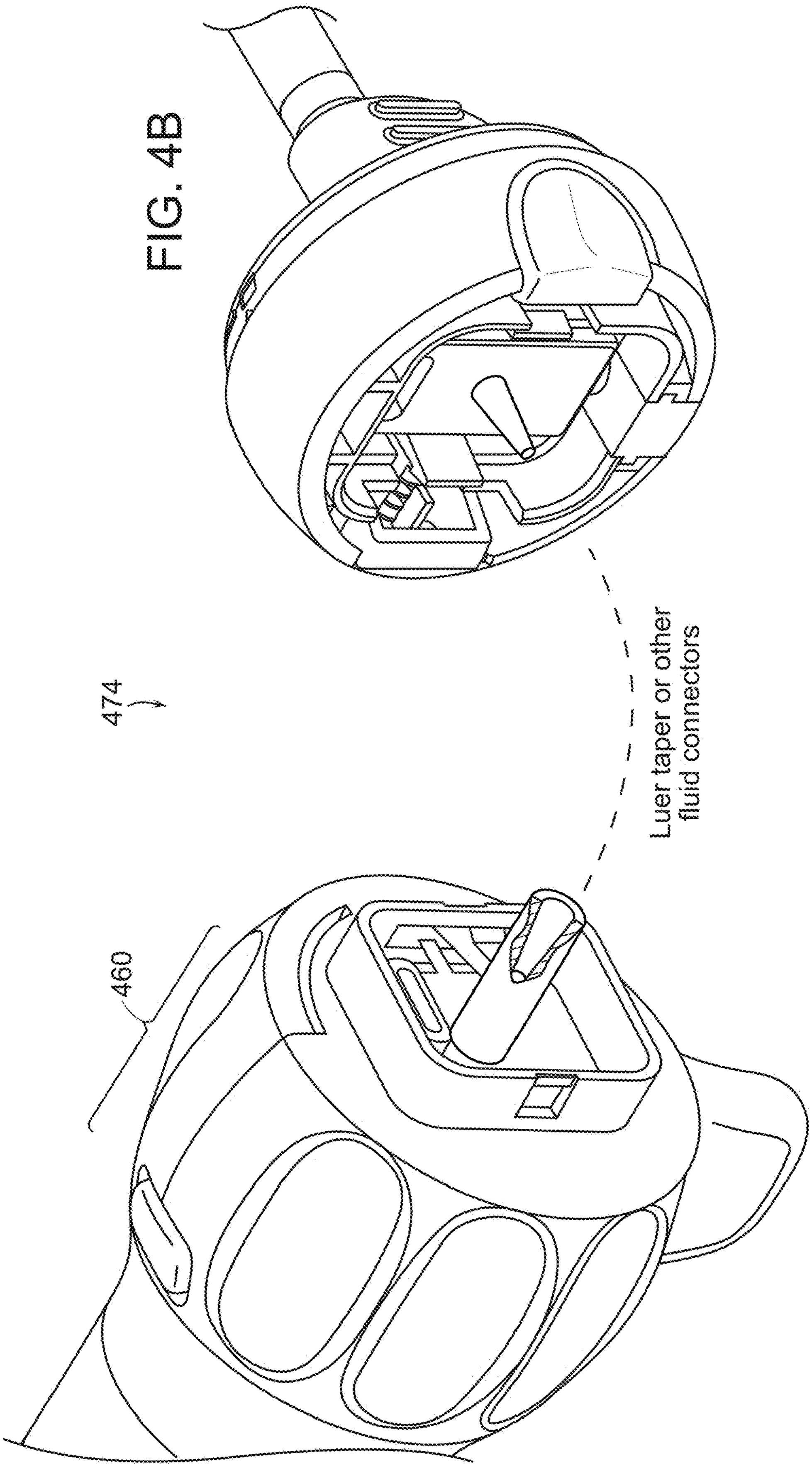

Referring to FIGS. 4A and 4B, needle/scope 100 may be structured to permit detachment of a needle/shaft/scope portion 110, 120, 470 from the needle/scope's handle 472. A camera or image sensor 122 at the tip of shaft 110, any panning mechanism, illumination, power and signal connectors, and fluid flow channels may be in the disposable shaft 470. Handle 472 may be designed to be reusable (which implies that handle 472 may be sterilizeable, for example in an autoclave or other sterilization device, or protectable by a disposable sterility sleeve). Joint 474 between the detachable shaft 470 and the reusable parts of handle 472 may be generally distal within the handle (but not necessarily at the distal-most end). The replaceable shaft portion 110, 120, 470 may be disposable, along with a disposable portion of the handle that is disposable with shaft.

The disposable cap, as this distal-most portion of the handle, may serve as a mounting base for shafts 110, 120, and may disconnect from the remainder 472 of the handle. This disposable cap portion 470 (along with shafts 110, 120 and componentry inside) may be disposable.

Rotation collar 460 may have surface features to allow a surgeon to rotate the rotation collar 460 about the central axis of the handle, that is, about the roll axis of shafts 110, 120. During the injection procedure, insertion shaft 110, 120, disposable cap 470 and rotation collar 460 may be locked to rotate with each other, so that rotating rotation collar 460 effects rotation of the disposable cap 470 and shafts 110, 120.

Proximal stationary handle has a shell surrounding componentry within the handle. The outer diameter and outer surface of the handle may be designed to provide an easy and low-slip grip for a surgeon's hand. Joint 462 between the proximal handle and rotation collar may allow these two components to rotate relative to each other. In some cases, a circuit board and similar componentry inside proximal handle 472 may rotate with disposable cap 110, 120, 470 and rotation collar 460, inside proximal handle.

Disposable cap 110, 120, 470 and rotation collar 460 may be separable from each other at separation joint 474, so that disposable cap and shafts 110, 120, 470 may be disposable, while handle 472 and rotation collar 460 (and componentry inside them) are reusable.

At separation joint 474 between disposable portions 110, 120, 470 and the reusable portions 472 including rotation collar 472, three basic connections may be made:

- A rotation-locking coupling to hold the disposable portion 470 to the reusable portion 472. This coupling may have sufficient strength to transmit insertion and withdrawal forces, roll, pitch, and yaw torques, lateral forces, and similar forces from the proximal reusable handle 472 to the distal disposable portion 110, 120, 470, thereby to allow a physician to aim the illumination and/or camera as needed. Separation joint 474 between disposable portion 110, 120, 470 may lie generally toward the distal end of the handle. Disposable portion 110, 120, 470 may engage through flat force-transmittal surfaces at the center of joint 474 and around the circumferences, so that these forces are supported around the circumference of separable joint 474. One or more release buttons 146 may be pressed or squeezed to cause one or more locking snaps 148 to disengage. The mechanical connection may include a rotatable locking ring or other release/fixation mechanisms.
- An electrical connection to supply power to the illumination source and camera, and to carry optical signals back from camera 122 to the processing board 364 in handle and display system outside needle/scope 100. The disconnectable electrical connections for power and signal may be effected by a USB-C connector mini HDMI connector, or similar connector that can maintain signal integrity for high speed signals. If illumination is conveyed by optical fiber, joint 474 may include an optical connector.
- A disconnectable connection to any panning mechanism for camera 122 may be effected by a physical connector, such as a linkage.

One or more fluid hoses for injectable liquid or inflation gas (or two hoses, one for the injectable fluid and one for gas) may enter through disposable cap, so that the entire set of fluid tubing for the irrigation/inflation channel may be disposable with the disposable shaft portion. In other cases, a fluid hose may enter the proximal end of the scope, and disconnectable fluid connections within joint for fluid inflow and outflow may be effected by gaskets, O rings, and the like. Alternatively, connectors for the hoses may be outboard of needle/scope 100 itself, either near needle/scope 100 (for applications where it may be desirable to allow "quick change" replacement of the insertion shaft in the course of a single procedure), or far from needle/scope 100, typically at the receptacle for waste fluid, to ease disposal of all hoses that are potentially contaminated by contact with the patient.

Disposable portion 110, 120, 470 may be designed to facilitate disposability of components that come into contact with bodily fluids. Because sterilization is often imperfect, patient safety may be improved by disposing of components that have come into contact with patient bodily fluids. To improve sterilizability, it may desirable to reduce componentry in the disposable component 110, 120 so that cost of the disposable component may be reduced, and to reduce surface features and crevices that may be difficult to sterilize. Thus, the lens, image sensor 122, illumination LED 250, panning mechanism, and shaft may be disposable. In addition, because shafts 110, 120 are used for fluid inflow and outflow, and are disposable, sealing against bodily fluids may be unnecessary.

Various replaceable components 110, 120, 470 may have different instruments at their tip. For example, various replaceable shafts may have cameras oriented at 0° (directly on-axis), 30°, 45°, 70°, and 90°.

Further features of a partially disposable, partially reusable device are described in U.S. Pub. No. 2019/0374095 A1, incorporated by reference Shaft 110 may also carry power wires to the illumination LED and the camera, and carry signal wires that carry an optical signal back from the camera to electronics in the reusable portion 472 of the handle. Electrical power to the camera may be supplied over conductors in a flexible cable or on a printed circuit board (flexible or rigid), and insulated with a conformal and insulating coating such as parylene.

This same flexible circuit board may have signal conductors for the video signal from the camera. The video signal may be transmitted from the camera to the handle using any video signal protocol, for example, MIPI (Mobile Industry Processor Interface) or HDMI. Parylene may also improve biocompatibility.

Shaft 120 may also carry cables or other mechanical elements to control panning of the camera.

Referring to FIGS. 4A and 4B, rotation collar may have various features that make rotation easy. For example, depressions may provide a good grip for fingers for light roll torque. A fin may provide greater leverage for greater roll torque, and may also provide a fixed rotational point of reference.

If camera 122 is pannable or has other controllable features, there may be a control (for example, a lever, or a touch-slide panel, etc.) on the handle to control that adjustment of the camera.

Electrical connectors such as USB-C or mini-HDMI connectors may be used to connect the camera to a circuit board interior to the handle.

Rotation-locking coupling may lock disposable cap in rotational relationship to rotation collar. Various rigid and resilient features may lock them together for other forces and torques, and release buttons may permit them to disengage to allow replacement of disposable cap.

The reusable portion 472 may contain a number of components, typically components that have only incidental patient contact (and therefore present less risk of cross-infection), are higher in cost (and therefore desirably reusable), and either sterilizeable or may be covered by a sterility sleeve. For example, reusable portion 472 may hold power transformers, signal amplifiers, controls for the illumination LED and camera, a mechanical control for panning the camera, rotation sensors for righting of an image from the camera, and the like. The handle may also include connections to external sources and destinations of power, signal, fluid, and the like.

For clarity of explanation, the above description has focused on a representative sample of all possible embodiments, a sample that teaches the principles of the invention and conveys the best mode contemplated for carrying it out. The invention is not limited to the described embodiments. Well known features may not have been described in detail to avoid unnecessarily obscuring the principles relevant to the claimed invention. Throughout this application and its associated file history, when the term "invention" is used, it refers to the entire collection of ideas and principles described; in contrast, the formal definition of the exclusive protected property right is set forth in the claims, which exclusively control. The description has not attempted to exhaustively enumerate all possible variations. Other undescribed variations or modifications may be possible. Where multiple alternative embodiments are described, in many cases it will be possible to combine elements of different embodiments, or to combine elements of the embodiments described here with other modifications or variations that are not expressly described. A list of items does not imply that any or all of the items are mutually exclusive, nor that any or all of the items are comprehensive of any category, unless expressly specified otherwise. In many cases, one feature or group of features may be used separately from the entire apparatus or methods described. Many of those undescribed alternatives, variations, modifications, and equivalents are within the literal scope of the following claims, and others are equivalent. The claims may be practiced without some or all of the specific details described in the specification. In many cases, method steps described in this specification can be performed in different orders than that presented in this specification, or in parallel rather than sequentially, or in different computers of a computer network, rather than all on a single computer.

The invention claimed is:

1. A method, comprising the steps of:

piercing a patient with an injection needle shaft of an injection needle assembly, the needle shaft having a point designed to pierce flesh of a living body, and having a fluid passage therethrough designed for delivery of a therapeutic injection agent at a delivery site within the body, the delivery site to be reached by piercing, the delivery site being a site of a pathology at which a therapeutic injection agent is to be delivered via the fluid passage, the outer diameter of the needle shaft being no more than about 2.1 mm;

the needle shaft surrounding solid state illumination circuitry and an imaging sensor designed to provide illumination and imaging, and arranged for illuminating and viewing the delivery site reached by piercing;

the injection needle assembly including one or more reservoirs for the therapeutic injection agent and controls designed to administer the agent without fluid tubes flowing externally to the injection needle assembly; and wireless transmission circuitry designed to transmit video signal from the imaging sensor to a display monitor without transmission wires connected to the injection needle assembly;

when the point of the needle shaft reaches the delivery site, passing inflation gas through a passage of the needle shaft at a pressure designed to expand a space around the delivery site and to dry the delivery site;

extending the imaging sensor forward through the needle shaft, sufficiently to create a field of view for the imaging sensor wider than the field of view available during the piercing;

rotating the imaging sensor and illumination circuitry around a longitudinal axis of the needle shaft, a rotation or orientation sensor rotationally affixed to the imaging sensor being designed to produce a signal that encodes angular rotation of the imaging sensor, and processing video from the imaging sensor and the encoded angular rotation signal together in image-righting circuitry to compute a corrected video signal that corrects the video signal for rotation to present a video signal consistently oriented relative to a frame of reference of a user of the injection needle assembly;

the injection needle assembly designed with all component parts either disposable or configured to be readily sterilized between uses.

2. The method of claim 1, wherein the imaging sensor has an axis of view offset from the axis of the needle shaft.

3. The method of claim 2:

the imaging sensor's axis of view is parallel to the axis of the needle shaft;

the injection needle assembly further comprising a lens designed to refract an image received by the imaging sensor off the axis of the needle shaft.

4. The method of claim 2, wherein:

the angle of offset is between about 250 and about 35°.

5. The method of claim 2, wherein:

the angle of offset is between about 65° and about 75°.

6. The method of claim 1, wherein:

a controller for the injection needle assembly further comprises circuitry designed to receive the encoded angular rotation signal and the video signal from the imaging sensor, and to compute the corrected video signal that corrects the video signal for rotation to present the video signal consistently oriented relative to the frame of reference of a user of the injection needle assembly.

7. The method of claim 1, wherein:

the injection needle assembly further comprises fluid tubes flowing externally to one or more reservoirs for inflation gas, and further comprises controls designed to administer the inflation gas.

8. The method of claim 1, wherein:

the needle shaft further comprises the piercing point distal from the imaging sensor designed to pierce flesh and to simultaneously provide protection of the imaging sensor from the flesh and its fluids, and to allow an image of the flesh to reach the imaging sensor.

9. The method of claim 1, wherein:

the outer diameter of the needle shaft is no more than about 1.66 mm.

10. The method of claim 1, wherein:

the outer diameter of the needle shaft is no more than about 1.28 mm.

11. The method of claim 1, wherein:

the injection needle assembly further comprises a handle, a proximal portion of the handle having electronics for drive of the illumination circuitry and to receive imaging signal from the imaging circuitry, the proximal handle portion being designed to permit sterilization between uses; and a separation joint between the proximal handle portion and the needle shaft designed to separably connect the needle shaft to the proximal handle portion:

when connected, the joint designed to provide mechanical force transfer between a surgeon's hand to the needle shaft, including stiffness in bending across the separation joint to transfer pitch and yaw torques across the separation joint, and electrical connectivity between the proximal handle circuitry and the illumination circuitry and imaging sensor.

12. The method of claim 1, wherein:

the imaging sensor is slideable within the needle shaft to permit the imaging sensor to be retracted behind the point during the piercing, and to be extended beyond the point to obtain a wider field of view.

13. An injection needle assembly, comprising:

a needle shaft with a point designed to pierce flesh of a living body, and having fluid passage means therethrough designed for delivery of a therapeutic injection agent at a delivery site within the body, the delivery site to be reached by piercing, the delivery site being a site of a pathology at which the therapeutic injection agent is to be delivered via the fluid passage, the outer diameter of the needle shaft being no more than about 2.1 mm; and illumination emitter means and solid state imaging sensor means designed to provide illumination and imaging, and arranged for illuminating and viewing the delivery site reached by piercing;

one or more reservoir means for the therapeutic injection agent and controls designed to administer the therapeutic injection agent without fluid tubes flowing externally to the injection needle assembly;

one or more reservoirs means for inflation gas and controls designed to administer the inflation gas;

and the needle shaft having a fluid passage through which inflation gas passes at a pressure designed to expand a space around the delivery site and to dry the delivery site;

wireless transmission means for transmitting video signal from the imaging sensor means to a display monitor without transmission wires connected to the injection needle assembly;

the injection needle assembly designed with all component parts either disposable or configured to be readily sterilized between uses.

14. An injection needle assembly, comprising:

a needle shaft with a point designed to pierce flesh of a living body, and having a fluid passage therethrough designed for delivery of a therapeutic injection agent at a delivery site within the body, the delivery site to be reached by piercing, the delivery site being a site of a pathology at which the therapeutic injection agent is to be delivered via the fluid passage, the outer diameter of the needle shaft being no more than about 2.1 mm;

an illumination emitter and an imaging sensor designed to provide illumination and imaging, and arranged for illuminating and viewing the delivery site reached by piercing;

the needle shaft having a passage through which pressurized inflation gas passes at a pressure designed to expand a space around the delivery site and to dry the injection site;

one or more reservoirs for storing the therapeutic injection agent and a controller designed to administer the therapeutic injection agent to the delivery site without for the therapeutic injection agent located externally to the injection needle assembly;

one or more reservoirs for storing the inflation gas and controls designed to administer the inflation gas; and wireless transmission circuitry designed to transmit video signal from the imaging sensor to a display monitor without transmission wires connected to the injection needle assembly;

the injection needle assembly designed with all component parts either disposable or configured to be readily sterilized between uses.

15. The injection needle assembly of claim 14, wherein the imaging sensor has an axis of view offset from the axis of the needle shaft.

16. The injection needle assembly of claim 15, wherein: the angle of offset is between about 250 and about 35°.

17. The injection needle assembly of claim 15, wherein: the angle of offset is between about 65° and about 75°.

18. The injection needle assembly of claim 15, wherein:

the imaging sensor's axis of view is parallel to the axis of the needle shaft;

and further comprising a lens designed to refract an image received by the imaging sensor off the axis of the needle shaft.

19. The injection needle assembly of claim 14, further comprising:

a rotation or orientation sensor designed to produce a signal that encodes angular rotation of the imaging sensor.

20. The injection needle assembly of claim 19, further comprising:

circuitry designed to receive the encoded angular rotation signal and the video signal from the imaging sensor, and to compute a corrected video signal that corrects the video signal for rotation to present a video signal consistently oriented relative to a frame of reference of a user of the injection needle assembly.

21. The injection needle assembly of claim 14:

the injection needle assembly further designed to extend the imaging sensor forward through the needle shaft, sufficiently to create a field of view for the imaging sensor wider than the field of view available during the piercing;

the injection needle assembly further designed to, when a user rotates the imaging sensor and illumination circuitry around a longitudinal axis of the needle shaft, produce a signal that encodes angular rotation of the imaging sensor from a rotation or orientation sensor rotationally affixed to the imaging sensor, and to process video from the imaging sensor and the encoded angular rotation signal together in image-righting circuitry to compute a corrected video signal that corrects the video signal for rotation to present a video signal consistently oriented relative to a frame of reference of a user of the injection needle shaft.

22. The injection needle assembly of claim 14, further comprising:

the one or more reservoirs for inflation gas and controls designed to administer the inflation gas without fluid tubes flowing externally to the injection needle assembly.

23. The injection needle assembly of claim 14, further comprising:

the piercing point distal from the imaging sensor designed to pierce flesh and to simultaneously provide protection to the imaging sensor from the flesh and its fluids, and to allow an image of the flesh to reach the imaging sensor.

24. The injection needle assembly of claim 14, wherein:

the outer diameter of the needle shaft is no more than about 1.66 mm.

25. The injection needle assembly of claim 14, wherein:

the outer diameter of the needle shaft is no more than about 1.28 mm.

26. The injection needle assembly of claim 14, further comprising:

a handle, a proximal portion of the handle having electronics for drive of an illumination circuitry and to receive imaging signal from an imaging circuitry, the proximal handle portion being designed to permit sterilization between uses; and a separation joint between the proximal handle portion and the needle shaft designed to separably connect the needle shaft to the proximal handle portion:

when connected, the joint designed to provide mechanical force transfer between a surgeon's hand to the needle shaft, including stiffness in bending across the separation joint to transfer pitch and yaw torques across the separation joint, and electrical connectivity between electronics in the proximal portion of the handle and the illumination circuitry and imaging sensor.

27. The injection needle assembly of claim 14, wherein:

the imaging sensor is slideable within the needle shaft to permit the imaging sensor to be retracted behind the point during the piercing, and to be extended beyond the point to obtain a wider field of view.

* * * * *